United States Patent [19]
Boesch

[11] 3,935,315
[45] Jan. 27, 1976

[54] INSECTICIDAL AND ACARICIDAL PHENYLHYDRAZONE DERIVATIVES

[75] Inventor: Roger Boesch, Vitry-sur-Seine, France

[73] Assignee: Rhone-Poulenc S.A., Paris, France

[22] Filed: Apr. 25, 1974

[21] Appl. No.: 464,213

Related U.S. Application Data

[62] Division of Ser. No. 363,651, May 24, 1973, Pat. No. 3,847,987.

[30] Foreign Application Priority Data

May 26, 1972  France .............................. 72.18895
Mar. 19, 1973  France .............................. 73.09754

[52] U.S. Cl. ............................ 424/327; 260/326.5
[51] Int. Cl.$^2$ ............................................ A01N 9/20
[58] Field of Search ................. 424/327; 260/566 B

[56] References Cited
UNITED STATES PATENTS

| | | | |
|---|---|---|---|
| 3,150,151 | 9/1964 | Urbschat et al. ................ | 260/326.5 |
| 3,636,112 | 1/1972 | Draber ............................ | 260/566 B |
| 3,786,131 | 1/1974 | Buchel et al. ..................... | 424/304 |
| 3,809,675 | 5/1974 | Hansen ........................... | 260/45.9 R |

OTHER PUBLICATIONS

Chemistry of Organic Compounds (Textbook) Noller, p. 234; 3rd Ed., 1965.

*Primary Examiner*—Leonard Schenkman
*Attorney, Agent, or Firm*—Stevens, Davis, Miller & Mosher

[57] ABSTRACT

Phenylhydrazone derivatives of the formula:

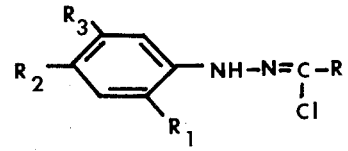

wherein R represents alkyl containing 1 to 4 carbon atoms, and two of the symbols $R_1$, $R_2$ and $R_3$ represent a halogen atom and the third represents a halogen atom or a nitro radical, are new compounds possessing insecticidal and acaricidal properties.

13 Claims, No Drawings

INSECTICIDAL AND ACARICIDAL PHENYLHYDRAZONE DERIVATIVES

This is a division of application Ser. No. 363,651, filed May 24, 1973 now U.S. Pat. No. 3,847,987.

This invention relates to new phenylhydrazone derivatives, to a process for their preparation and to compositions containing them.

The phenylhydrazone derivatives of the present invention are those of the general formula:

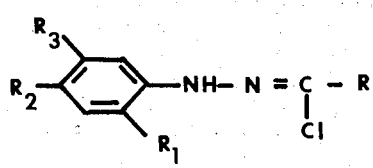
I wherein R represents a straight- or branched-chain alkyl radical containing 1 to 4 carbon atoms, and two of the symbols $R_1$, $R_2$ and $R_3$ represent a halogen (preferably chlorine) atom and the third symbol represents a halogen (preferably chlorine) atom or a nitro radical.

According to a feature of the present invention, the phenylhydrazone derivatives of general formula I are prepared by the action of a chlorinating agent, such as phosphorus pentachloride, phosphorus oxychloride or thionyl chloride, on a phenylhydrazide of the general formula:

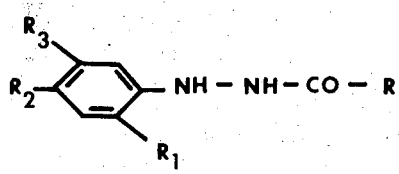
II wherein R, $R_1$, $R_2$ and $R_3$ are as hereinbefore defined.

Preferably phosphorus pentachloride is used as the chlorinating agent and the reaction can then be represented schematically in the following manner:

1)
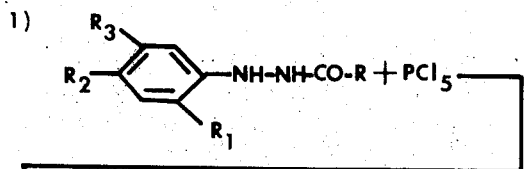

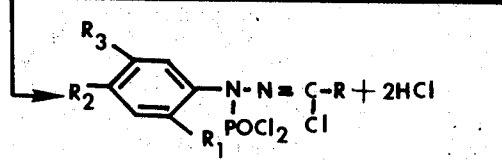

2)
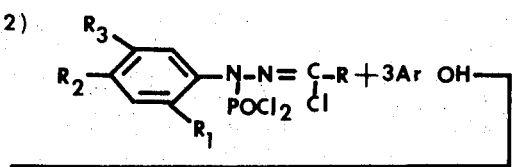

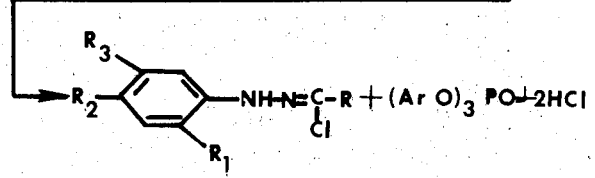

wherein the various R symbols are as hereinbefore defined, and Ar represents a phenyl radical which is optionally substituted, for example, by an alkyl radical.

Conversion of the grouping —NH—CO—R in the phenylhydrazides of general formula II into a grouping

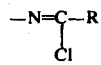

is generally effected by heating the phenylhydrazide of general formula II and phosphorus pentachloride in an inert organic solvent such as carbon tetrachloride, preferably at the reflux temperature of the solvent employed, e.g. about 80°C. Decomposition of the phosphorylated complex obtained can be effected by heating with a phenol in the same inert organic solvent.

When thionyl chloride is employed as the chlorinating agent the reaction can be represented schematically as follows:

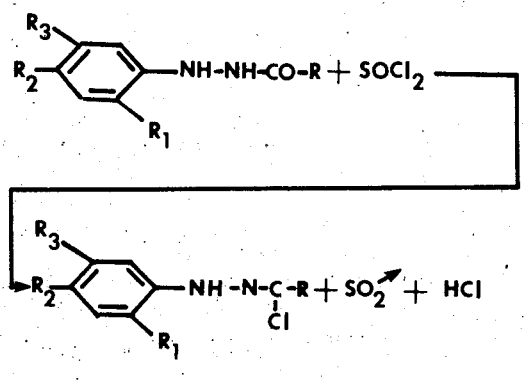

wherein the various R symbols are as hereinbefore defined. Generally the reaction is effected by heating the reactants in an inert organic solvent such as carbon tetrachloride, preferably at the reflux temperature of the solvent employed e.g. about 80°C.

The phenylhydrazides of general formula II, wherein R is as hereinbefore defined, $R_1$ represents a nitro radical and $R_2$ and $R_3$ each represent a halogen atom, can be obtained by the action of a hydrazide of the general formula:

$$R - CO - NH - NH_2 \qquad III$$

(wherein R is as hereinbefore defined) on a nitrobenzene of the general formula:

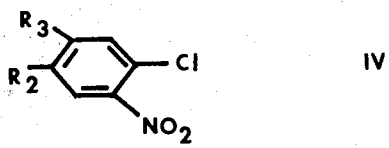
IV wherein $R_2$ and $R_3$ represent halogen atoms.

The phenylhydrazides of general formula II, wherein $R_1$ and $R_2$ each represent a halogen atom and $R_3$ represents a halogen atom or a nitro radical, can be obtained by the action of an acid of the general formula:

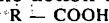  V (wherein R is as hereinbefore defined), or a derivative of the acid, such as a halide or the anhydride, on a phenylhydrazine of the general formula:

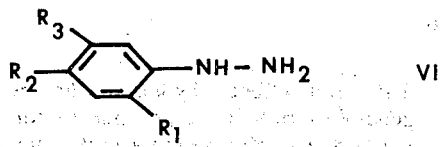  VI wherein $R_1$, $R_2$ and $R_3$ are as hereinbefore defined. The reaction is generally carried out in an inert organic solvent such as methylene chloride, ethyl acetate or an aromatic hydrocarbon such as benzene.

The phenylhydrazines of general formula VI can be obtained by diazotization of the corresponding anilines and reduction of the resulting diazonium salts.

The phenylhydrazone derivatives of general formula I obtained by the afore-described process can optionally be purified by application of physical methods such as crystallisation or chromatography.

The new compounds of general formula I possess interesting insecticidal and acaricidal properties.

The insecticidal activity is manifest more particularly against diptera (Musca domestica), coleoptera (Tribolium confusum) and lepidoptera (Plutella maculipennis caterpillars) at amounts between 1 and 100 grams of active material per hectoliter of liquid diluent. The acaricidal activity is interesting against phytophagus acarids (Tetranychus telarius) at amounts between 1 and 100 grams of active substance per hectoliter of liquid diluent. At amounts between 10 and 200 grams of active material per hectoliter of liquid diluent the phenylhydrazone derivatives of general formula I show a considerable ovicidal activity.

Compounds of general formula I of outstanding importance are those in which $R_1$ and $R_3$ represent chlorine atoms, or one of $R_1$ and $R_3$ represents a chlorine atom and the other symbol represents a nitro radical, and $R_2$ represents a chlorine atom, for example 1-(4,5-dichloro-2-nitrophenyl-hydrazono)-1-chloro-2,2-dimethylpropane, 1-(2,4-dichloro-5-nitrophenyl-hydrazono)-1-chloro-2,2-dimethylpropane, 1-(2,4,5-trichlorophenyl-hydrazono)-1-chloropropane, 1-(2,4,5-trichlorophenyl-hydrazono)-1-chloro-2,2-dimethylpropane, 1-(2,4,5-trichlorophenyl-hydrazono)-1-chloroethane, 1-(2,4,5-trichlorophenylhydrazono)-1-chlorobutane and 1-(2,4,5-trichlorophenylhydrazono)-1-chloro-2-methylpropane.

According to a further feature of the present invention, there are provided insecticidal and acaricidal compositions which contain, as the active ingredient, at least one of the phenylhydrazone derivatives of general formula I in association with one or more diluents or adjuvants compatible with the phenylhydrazone derivative(s) and suitable for use in agriculture.

These compositions can optionally contain other compatible pesticides such as fungicides (e.g. maneb). Preferably the compositions contain between 0.005% and 80% by weight of phenylhydrazone derivative.

The compositions may be solid if there is employed a powdered solid compatible diluent such as talc, calcined magnesia, kieselguhr, tricalcium phosphate, powdered cork, adsorbent charcoal, or a clay such as kaolin or bentonite. These solid compositions are preferably prepared by grinding the phenylhydrazone derivative with the solid diluent, or by impregnating the solid diluent with a solution of the phenylhydrazone derivative in a volatile solvent, evaporating the solvent, and if necessary grinding the product so as to obtain a powder.

Instead of a solid diluent, there may be used a liquid in which the phenylhydrazone derivative is dissolved or dispersed. The compositions may thus take the form of suspensions, emulsions or solutions in organic or aqueous-organic media, for example aromatic hydrocarbons such as toluene or xylene, mineral, animal or vegetable oils, or acetophenone, or mixtures of these diluents. The compositions in the form of suspensions, emulsions or solutions may contain wetting, dispersing or emulsifying agents of the ionic or non-ionic type, for example sulphoricinoleates, quaternary ammonium derivatives or products based on condensates of ethylene oxide such as the condensates of ethylene oxide with octylphenol, or fatty acid esters of anhydrosorbitols which have been rendered soluble by etherification of the free hydroxyl groups by condensation with ethylene oxide. It is preferable to use agents of the non-ionic type because they are not sensitive to electrolytes. When emulsions are required the phenylhydrazone derivatives may be used in the form of self-emulsifying concentrates containing the active substance dissolved in the emulsifying agent or in a solvent containing an emulsifying agent compatible with the phenylhydrazone derivative and solvent, a simple addition of water to such concentrates producing compositions ready for use.

The phenylhydrazone derivatives of general formula I are preferably employed for insecticidal and acaricidal purposes in quantities of 10 to 100 g. per hectoliter of water, but lower concentrations can also be used effectively.

The following Example illustrates the preparation of phenylhydrazone derivatives of general formula I.

EXAMPLE 1

A suspension of 1-(4,5-dichloro-2-nitrophenyl)-2-trimethylacetyl-hydrazine (739 g.) and phosphorus pentachloride (517 g.) in carbon tetrachloride (4.8 liters) is heated until the evolution of gas ceases, the reaction mixture being taken progressively to the reflux temperature. To the solution obtained there is added, after cooling to 20°C., a solution of phenol in carbon tetrachloride (3.36 liters) containing 2.36 moles of phenol per liter. The reaction mixture is then heated at the reflux temperature until the evolution of gas finishes. It is then cooled to 20°C., filtered and the resulting solution is concentrated under reduced pressure (20 mm. Hg.) at 60°C. The residue is purified by chromatography on "Kieselgel", elution being effected with a mixture of heptane and diethyl ether (9.5 – 0.5 by volume). After recrystallisation from isopropanol and then heptane, there is obtained 1-(4,5-dichloro-2-nitrophenyl-hydrazono)-1-chloro-2,2-dimethylpropane (498g.) melting at 99°–100°C.

The 1-(4,5-dichloro-2-nitrophenyl)-2-trimethylacetyl-hydrazine, m.p. 153°C., employed as starting material can be obtained by the action of trimethylacetylhydrazine on 2,4,5-trichloronitrobenzene in N-methylpyrrolid-2-one.

By proceeding as described in the foregoing Example and starting with appropriate phenylhydrazides of general formula II, there are prepared the following phenylhydrazone derivatives conforming to general formula I:

1-(2,4-dichloro-5-nitrophenyl-hydrazono)-1-chloro-2,2-dimethylpropane, m.p. 109°C.;
1-(2,4,5-trichlorophenyl-hydrazono)-1-chloropropane, solidification point 40°C.;
1-(2,4,5-trichlorophenyl-hydrazono)-1-chloro-2,2-dimethylpropane, m.p. 76°C.;
1-(2,4,5-trichlorophenyl-hydrazono)-1-chloroethane, m.p. 104°C.;
1-(2,4,5-trichlorophenyl-hydrazono)-1-chlorobutane, solidification point 34°C., and
1-(2,4,5-trichlorophenyl-hydrazono)-1-chloro-2-methylpropane, m.p. 57°C.

The following Examples illustrate compositions according to the invention.

EXAMPLE 2

5 g. of a condensation product of octylphenol and ethylene oxide containing 10 molecules of ethylene oxide per molecule of octylphenol are added to 20 g. of 1-(4,5-dichloro-2-nitrophenyl-hydrazono)-1-chloro-2,2-dimethylpropane, and a mixture of equal volumes of toluene and acetophenone are added until the mixture reaches 100 cc.

The solution thus obtained is utilised after suitable dilution with water to destroy acarids. According to the effect required, concentrations of 10 to 100 g. of phenylhydrazone derivative per hectoliter of water give good results.

EXAMPLE 3

To 50 parts of 1-(4,5-dichloro-2-nitrophenylhydrazono)-1-chloro-2,2-dimethylpropane there are added 1 part of Tween 80 (the mono-oleate of a polyoxyethylene derivative of sorbitol), 20 parts of calcium lignosulphite and 29 parts of kieselguhr. After grinding and sieving, the powder obtained is utilised after dilution with water to destroy acarids.

The parts referred to above are parts by weight.

I claim:

1. An insecticidal and acaricidal composition suitable for agricultural use containing 0.005 to 80% by weight of a phenylhydrazone derivative of the formula:

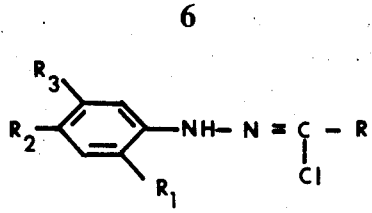

wherein R represents alkyl of 1 through 4 carbon atoms, and two of the symbols $R_1$, $R_2$ and $R_3$ represent halogen and the third represents halogen or nitro, and a compatible diluent therefor.

2. A composition according to claim 1 in which the diluent is water and the composition contains 10 to 100 g. of phenylhydrazone derivative per hectoliter of water.

3. A composition according to claim 1 which contains a wetting agent.

4. A composition according to claim 3 in which the wetting agent is a non-ionic compound.

5. A composition according to claim 1 wherein the halogen atoms are chlorine.

6. A composition according to claim 1 wherein $R_1$ and $R_3$ represent chlorine, or one of $R_1$ and $R_3$ represents chlorine and the other symbol represents nitro, and $R_2$ represents chlorine.

7. A composition according to claim 1 wherein the phenylhydrazone derivative is 1-(4,5-dichloro-2-nitrophenylhydrazono)-1-chloro-2,2-dimethylpropane.

8. A composition according to claim 1 wherein the phenylhydrazone derivative is 1-(2,4-dichloro-5-nitrophenylhydrazono)-1-chloro-2,2-dimethylpropane.

9. A composition according to claim 1 wherein the phenylhydrazone derivative is 1-(2,4,5-trichlorophenylhydrazono)-1-chloropropane.

10. A composition according to claim 1 wherein the phenylhydrazone derivative is 1-(2,4,5-trichlorophenylhydrazono)-1-chloro-2,2-dimethylpropane.

11. A composition according to claim 1 wherein the phenylhydrazone derivative is 1-(2,4,5-trichlorophenylhydrazono)-1-chloroethane.

12. A composition according to claim 1 wherein the phenylhydrazone derivative is 1-(2,4,5-trichlorophenylhydrazono)-1-chlorobutane.

13. A composition according to claim 1 wherein the phenylhydrazone derivative is 1-(2,4,5-trichlorophenylhydrazono)-1-chloro-2-methylpropane.

* * * * *